United States Patent [19]

Ashkin et al.

[11] Patent Number: 4,893,886

[45] Date of Patent: Jan. 16, 1990

[54] NON-DESTRUCTIVE OPTICAL TRAP FOR BIOLOGICAL PARTICLES AND METHOD OF DOING SAME

[75] Inventors: Arthur Ashkin, Rumson; Joseph M. Dziedzic, Clark, both of N.J.

[73] Assignees: American Telephone and Telegraph Company, New York, N.Y.; AT&T Bell Laboratories, Murray Hill, N.J.

[21] Appl. No.: 98,120

[22] Filed: Sep. 17, 1987

[51] Int. Cl.$^4$ .............................................. G02B 27/00
[52] U.S. Cl. .................................................... 350/1.1
[58] Field of Search ...................................... 350/1.1

[56] References Cited

U.S. PATENT DOCUMENTS

| | | | |
|---|---|---|---|
| 3,710,279 | 1/1973 | Ashkin | 331/94.5 |
| 3,808,432 | 4/1974 | Ashkin | 250/251 |
| 3,808,550 | 4/1974 | Ashkin | 331/94.5 |
| 4,327,288 | 4/1982 | Ashkin et al. | 250/251 |

OTHER PUBLICATIONS

*Physical Review Letters*, vol. 24, No. 4, Jan. 26, 1970, "Acceleration and Trapping of Particles by Radiation Pressure", by A. Ashkin, pp. 156-159.
*Appl. Phys. Lett.*, vol. 19, No. 8, Oct. 15, 1971, "Optical Levitation by Radiation Pressure", by A. Ashkin et al., pp. 283-285.
*Physical Review Letters*, vol. 40, No. 12, Mar. 20, 1978, "Trapping of Atoms by Resonance Radiation Pressure", by A. Ashkin, pp. 729-732.
*Science*, vol. 210, No. 5, Dec. 5, 1980, "Applications of Laser Radiation Pressure", by A. Ashkin, pp. 1081-1088.
*Physical Review Letters*, vol. 57, No. 3, Jul. 21, 1986, "Experimental Observation of Optically Trapped Atoms", by Chu et al., pp. 314-317.
*Physical Review Letters*, vol. 41, No. 20, Nov. 13, 1978, "Observation of Focusing of Neutral Atoms by the Dipole Forces of Resonance-Radiation Pressure", by Bjorkholm et al., pp. 1361-1364.
*Applied Optics*, vol. 19, No. 5, Mar. 1, 1980, "Observation of Light Scattering from Nonspherical Particles Using Optical Levitation", by A. Ashkin et al., pp. 660-668.
*Optics Letters*, vol. 8, No. 10, Oct. 1983, "Stability of Radiation-Pressure Particle Traps: an Optical Earnshaw Theorem", by A. Ashkin et al., pp. 511-513.
*Physical Review Letters*, vol. 54, No. 12, Mar. 25, 1985, "Observation of Radiation-Pressure Trapping of Particles by Alternating Light Beams", by A. Ashkin et al., pp. 1245-1248.
*Optics Letters*, vol. 11, No. 5, May 1986, "Observation of a single-beam Gradient Force Optical Trap for Dielectric Particles", A. Ashkin et al., pp. 288-290.

*Primary Examiner*—Bruce Y. Arnold
*Attorney, Agent, or Firm*—Gregory C. Ranieri

[57] ABSTRACT

Biological particles are successfully trapped in a single-beam gradient force trap using an infrared laser. The high numerical aperture lens objective in the trap is also used for simultaneous viewing.

Several modes of trapping operation are presented.

5 Claims, 3 Drawing Sheets

NON-DESTRUCTIVE OPTICAL TRAP FOR BIOLOGICAL PARTICLES AND METHOD OF DOING SAME

TECHNICAL FIELD

This invention relates to trapping of particles using a single-beam gradient force trap.

BACKGROUND OF THE INVENTION

Single-beam gradient force traps have been demonstrated for neutral atoms and dielectric particles. Generally, the single-beam gradient force trap consists only of a strongly focused laser beam having an approximately Gaussian transverse intensity profile. In these traps, radiation pressure scattering and gradient force components are combined to give a point of stable equilibrium located close to the focus of the laser beam. Scattering force is proportional to optical intensity and acts in the direction of the incident laser light. Gradient force is proportional to the optical intensity and points in the direction of the intensity gradient.

Particles in a single-beam gradient force trap are confined transverse to the laser beam axis by a radial component of the gradient force. Stabilizing the particle along the axis direction of the trap is achieved by strongly focusing the laser beam to have the axial component of gradient force dominate the scattering force in the trap region.

In prior work using single-beam gradient force optical traps on dielectric particles, trapping was demonstrated with a visible light laser source ($\lambda = 514.5$ nm.) focused by a high numerical aperture lens objective. See A. Ashkin et al., *Optics Letters*, Vol. 11, p 288–90. The dielectric particles were closely spherical or spheroidal in shape and ranged in size from 10 $\mu$m diameter Mie glass spheres ($a >> \lambda$) down to 260 Angstrom diameter Rayleigh particles ($a \leq \leq \lambda$). Use of such regularly shaped particles in the Mie regime was desirable as taught in this and other articles.

For Mie particles, both the magnitude and direction of the forces depend on the particle shape. This restricts trapping to fairly simple shapes such as spheres, ellipsoids, or particles whose optical scattering varies slowly with orientation in the trap. In the Rayleigh regime, the particle acts as a dipole and the direction of force is independent of particle shape; only the magnitude of force varies with particle orientation.

It is not an insignificant result of the prior work that silica and other dielectric particles experienced varying amounts of irreversible optical damage from the trap. While it was suggested that the single-beam trap and the prior results would be extensible to biological particles, the resulting damage from exposure in the trap would destroy or significantly incapacitate the biological particles and render them useless. Also, since prior optical traps have been defined for quite regular-shaped, dielectric particles, their extension to biological particles is cast in doubt because regularity of shape is not an attribute of biological particles.

SUMMARY OF THE INVENTION

Biological particles are successfully trapped in a single-beam gradient force optical trap incorporating an infrared light source. Reproduction of trapped particles has been observed. After release from the trap, particles exhibit normal motility and continued reproductivity even after trapping for several life cycles at a high laser power of 160 mW.

In one embodiment, the higher numerical aperture lens objective in the single-beam gradient force trap is used for simultaneous viewing of the trapped biological particles.

Two single-beam gradient force optical traps are introduced into the same cell to permit three-dimensional manipulation of the biological particles.

BRIEF DESCRIPTION OF THE DRAWING

A more complete understanding of the invention may be obtained by reading the following description of a specific illustrative embodiment of the invention in conjunction with the appended drawing in which.

DETAILED DESCRIPTION

Single-beam gradient force optical traps are useful for confining, isolating, translating and manipulating at least one particle in a group of particles enclosed in a cell or hanging droplet or the like. Special problems surface when the particles are biological. For example, absorption of the optical energy in the trap by the confined particle may lead to particle annihilation or a significant loss of particle motility. Also, as the wavelength of the light beam is varied to avoid the aforementioned problem, the intensity of the optical trap may be sufficiently decreased so as to be rendered ineffective for the particles of interest. While the wavelength selected may be sufficient for effective operation of the optical trap, it may be at a wavelength which is absorbed by the medium surrounding the particles and, therefore, which leads to heat generation within the cell. Clearly, many factors must be considered when selecting the operating wavelength for the optical trap.

In the prior optical trap experiments reports in the literature, particle sensitivity has not been an issue. This is generally attributed to the fact that dielectric particles have homogeneous compositions and uniformly regular shapes so that it is straightforward to observe the effect of the trap on one particle or portion of a particle and accurately predict the effect on other particles or on other portions of the same dielectric particle. For biological particles, sensitivity of the particles is extremely important. Biological particles have heterogeneous compositions and irregular shapes. Hence, the effect of the trap on one part of a biological particle is in no way determinative of the effect in another portion of the same particle.

Figure 1:
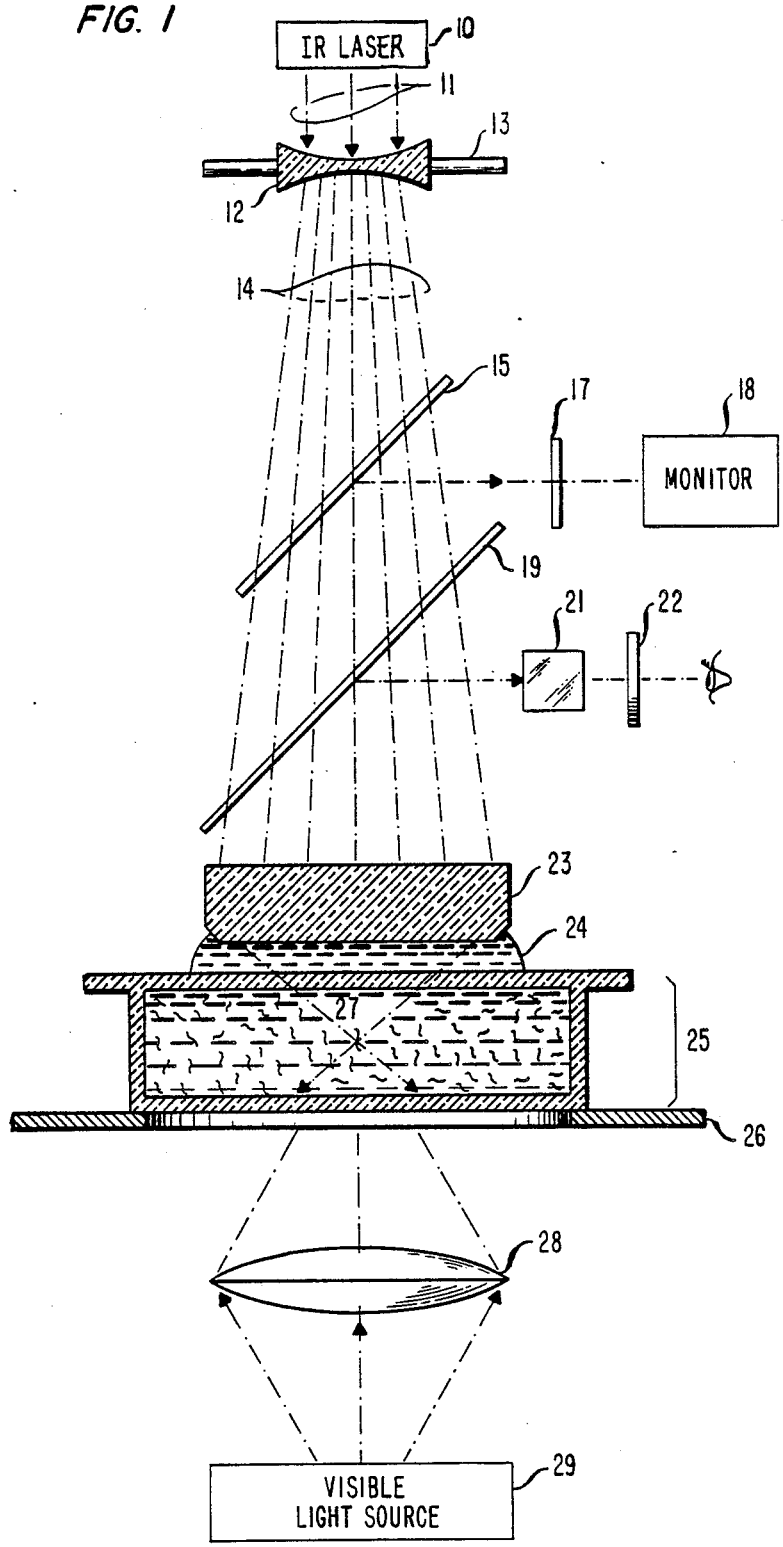
FIG. 1 is a cross-sectional schematic diagram of an embodiment of the invention.

FIG. 1 shows a cross-sectional schematic diagram of apparatus for creating a single-beam gradient force optical trap in accordance with the principles of this invention. IR laser 10 is a standard laser emitting a coherent light beam substantially in the infrared range of wavelengths, for example, 0.8 $\mu$m to 1.8 $\mu$m.

Light beam 11 from IR laser 10 impinges upon a combination of optics elements for focusing the light beam with a sufficient degree of convergence to form a single-beam gradient force optical trap for confining biological particles at a desired position. The combination of optics elements includes an adjustably mounted diverging lens 12 and a high convergence lens 23.

Lens 12 is adjustable in any of three dimensions (x, y, z) by manipulating adjustable mount 13. It is important that lens 12 expand that spot size of light beam 11 to cover a substantial area on the surface of lens 23. As shown in FIG. 1, diverging light beam 14 impinges on a large portion of the facing surface of lens 23 so that relatively high intensity of beam 14 fills the aperture of lens 23. In order to create the forces required for operation of the single-beam gradient force optical trap, it is desirable that lens 23 be capable of focusing to a spot size less than $\lambda$ approaching $\lambda/2$. In an example from experimental practice, lens 23 is a strong or high convergence water immersion microscope objective lens having a numerical aperture of approximately 1.25 (measured in water). wherein the numerical aperture is defined as the refractive index for the medium multiplied by the sine of the half angle covered by the converging light beam. Element 24 depicts the liquid (water or oil) in which lens 23 is immersed for improved optical coupling into cell 25.

The optical trap is shown within cell 25 with particle 27 captured in the trap. Particle 27 is suspended in a liquid medium such as water, for example, which is enclosed by cell 25. Cell 25 is a transparent enclosure for enclosing the suspended biological particles or a transparent slide from which particle containing droplets can be hung. In one example, cell 25 has dimensions of 1 cm.$\times$3 cm.$\times$100 $\mu$m.

The position of cell 25 is adjustable in three dimensions (x, y, z) by the use of adjustable mount 26. In practice, mount 26 is useful in locating and manipulating the biological particles.

Viewing of biological particles in the trap is accomplished directly or through the use of a monitor. While other types of viewing such as viewing directly in cell 25 are possible, it is an added feature of the present invention that the viewing is accomplished through the same lens objective which simultaneously creates the optical trap.

Illumination for viewing is provided by visible light source 29 and is projected through converging lens 28 onto the particles in the field of view. High resolution viewing occurs with the aid of lens 23 through which the visible light passes toward either the eyepiece 22 or the monitor 18. For direct viewing, visible light shown as a dashed line is reflected from beam splitter 19 to microscope eyepiece 21. Infrared blocking filter 22 is placed in front of eyepiece 21 to isolate the viewing optics (viewer's eye) from back reflections from cell 25. For monitoring, the visible light passes through beam splitter 19 and is reflected from beam splitter 15 toward infrared blocking filter 17 and finally monitor 18. Infrared blocking filter 17 isolates the monitor from back reflections from cell 25.

Figure 2:
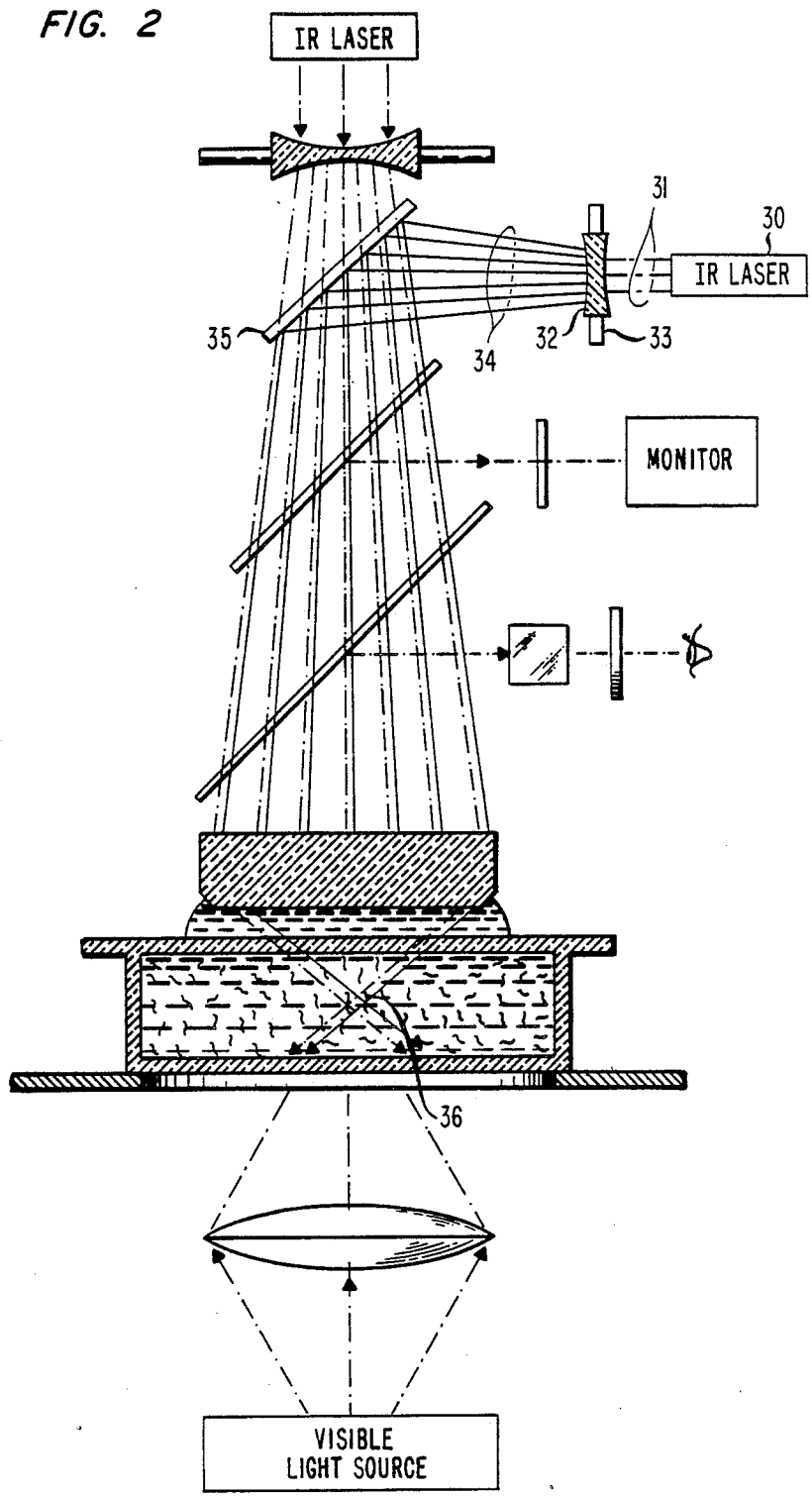
FIG. 2 is a cross-sectional schematic diagram of an embodiment of the invention employing two single-beam gradient force traps in one cell.

In FIG. 2, the apparatus shown in FIG. 1 is augmented by a second infrared laser source and optics to create a second single-beam gradient force optical trap in cell 25. Infrared laser source 30 generates light beam 31 impinging on adjustably mounted diverging lens 32. Lens 32 causes beam 31 to emerge in a diverging pattern as light beam 34. Adjustment of lens 32 is accomplished in three dimensions (x, y, z) via adjustable mount 33. Light beam 34 is reflected by mirror 35 which coincidently permits transmission of light beam 14. This would occur by judiciously choosing different wavelengths of operation for the separate laser sources. On the other hand, element 35 can be realized as a beam splitter which would reflect approximately half of the light beam incident thereon and transmit the remaining half. As shown in FIG. 2, light beam 34 is converged by lens 23 to form a second trap in cell 25. Particle 36 is confined in the second trap.

While not shown, it should now be apparent to those skilled in the art that a second trap may be created in the cell by utilizing an additional set of optics including another high convergence microscope. The second trap may be created from light entering the cell on the side opposite the beam for the first trap or, for that matter, at any angle to the beam for the first trap.

Manipulation or orientation of particles is achieved by grabbing each end of a rod-like particle, for example, and moving it at will.

In operation, it is necessary to move the trapped biological particles into the viewing plane. This is carried out by adjusting the position of the diverging lens or lenses. Similarly, translation, separation or isolation of the biological particles is easily affected by adjusting mount 26 by the desired amount.

Figure 3:
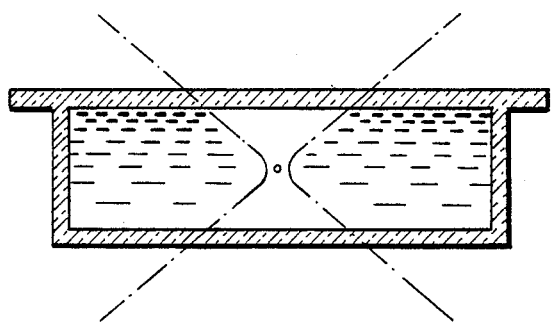
FIGS. 3 through 5 are schematic drawings of different modes of operation for an optical trap on particles in a cell.
Figure 4:
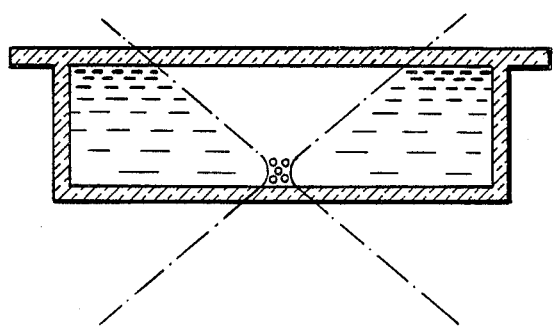
Figure 5:
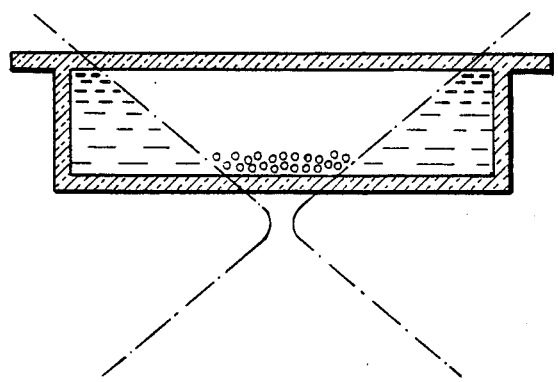

FIGS. 3 through 5 show several modes of operation for the same optical trap. FIG. 3 shows the conventional mode of operation in which the focus of the beam from lens 23 lies within cell 25 and the trapping action relies on the backward gradient component of the optical force. Depending on the size of the particles, it is possible to trap up to approximately four or five particles within the trap at one time.

Both modes shown in FIGS. 4 and 5 require less intensity than for the trap in FIG. 3. In FIG. 4, the bottom plate of cell 25 provides the backward trapping force and the gradient provides the transverse trapping force. It is possible to trap approximately twelve or more biological particles at one time. In FIG. 5, the scattering force of the focused light beam provides transverse confinement due to its inward direction; backward trapping is supplied by the bottom plate of cell 25. In the latter mode of operation, it is possible to trap significantly greater numbers of particles than for the modes shown in FIGS. 3 and 4.

Various biological particles have been isolated, confined and transported in this type of optical trap. For example, some biological particles successful trapped are tobacco mosaic viruses (See Ashkin et al., *Science*, Vol. 235, pp. 1517–20 (1987).), yeast, E. coli bacteria, blood cells containing hemoglobin, and complex cells or parts of cells containing chlorophyll structures.

In general, the biological particles investigated do not have the regular shape of the dielectric spheres studied earlier. For example, passive, string-like organisms were trapped wherein the organism was approximately 50 $\mu$m long and approximately 1 $\mu$m in diameter. In the case of tobacco mosaic virus, the particles resemble a cylinder about 200 angstroms in diameter and 3100 angstroms long.

It is a significant attribute of the present invention that particle motility is preserved and reproductivity of the particles is maintained. Reproduction by trapped biological particles has been observed with offspring remaining in the trap. In other words, the optical trap permits non-destructive manipulation of biological particles at optical powers approaching several hundred milliwatts.

It should be noted that the use of infrared light results in a lower intensity trap at the focal spot for the same laser power than for traps using visible light. However, the forces in the trap are approximately equal. Thus, the infrared trap has the added benefit over visible light traps of inducing less local heating in the focal spot.

What is claimed is:

1. Apparatus for generating a single-beam gradient force optical trap of particles, said apparatus comprising a laser for generating a light beam at a predetermined wavelength and means for focusing said light beam with sufficient convergence to form said optical trap in a predetermined region, said apparatus characterized in that said predetermined wavelength is substantially included in the infrared range of wavelengths between 0.8 $\mu$m and 1.8 $\mu$m inclusively, so that said trap non-destructively confines at least one biological particle.

2. Apparatus as defined in claim 1 wherein said focusing means includes a lens having a numerical aperture greater than 0.9.

3. Apparatus as defined in claim 1 further including means for varying a position of said predetermined region.

4. Apparatus for generating a single-beam gradient force optical trap of particles, said apparatus being comprised of a laser for generating a light beam at a predetermined wavelength and means for focusing said light beam with sufficient convergence to form said optical trap in a predetermined region, said apparatus characterized in that said predetermined wavelength is substantially included in the infrared range of wavelengths, so that said trap non-destructively confines at least one biological particle, said apparatus further including means for generating a second light beam substantially at the predetermined wavelength, said second light beam focused by said focusing means to form a second optical trap in a second predetermined region.

5. Apparatus as defined in claim 4 further including means for independently varying relative positions of the predetermined regions.

* * * * *